(12) United States Patent
Montag et al.

(10) Patent No.: US 8,812,079 B2
(45) Date of Patent: Aug. 19, 2014

(54) COMPENSATION FOR MAGNETIC DISTURBANCE DUE TO FLUOROSCOPE

(75) Inventors: Avram Dan Montag, Haifa (IL); Meir Bar-Tal, Haifa (IL); Tal Haim Bar-on, Kiryat Tivon (IL)

(73) Assignee: Biosense Webster (Israel), Ltd., Yokneam (IL)

( * ) Notice: Subject to any disclaimer, the term of this patent is extended or adjusted under 35 U.S.C. 154(b) by 889 days.

(21) Appl. No.: 12/975,915

(22) Filed: Dec. 22, 2010

(65) Prior Publication Data
US 2012/0165656 A1    Jun. 28, 2012

(51) Int. Cl.
*A61B 5/00*    (2006.01)
*A61B 5/06*    (2006.01)

(52) U.S. Cl.
CPC ...................................... *A61B 5/062* (2013.01)
USPC ............................ 600/424; 600/425; 600/427

(58) Field of Classification Search
USPC .......... 600/410, 411, 421–425, 427; 128/898; 606/130
See application file for complete search history.

(56) References Cited

U.S. PATENT DOCUMENTS

| | | | |
|---|---|---|---|
| 5,767,669 A | 6/1998 | Hansen et al. | |
| 6,147,480 A | 11/2000 | Osadchy et al. | |
| 6,714,008 B1 | 3/2004 | Holmes et al. | |
| 7,062,391 B2 * | 6/2006 | Wilson ............................ | 702/64 |
| 7,532,997 B2 | 5/2009 | Li et al. | |
| 7,657,075 B2 | 2/2010 | Viswanathan | |
| 7,689,019 B2 | 3/2010 | Boese et al. | |
| 7,751,865 B2 * | 7/2010 | Jascob et al. .................. | 600/424 |
| 2002/0172328 A1 | 11/2002 | Dekel | |
| 2004/0034515 A1 | 2/2004 | Bar Tal et al. | |
| 2005/0107687 A1 | 5/2005 | Anderson | |
| 2007/0055125 A1 | 3/2007 | Anderson et al. | |
| 2008/0079421 A1 | 4/2008 | Jensen | |
| 2008/0183064 A1 | 7/2008 | Chandonnet et al. | |
| 2009/0010540 A1 | 1/2009 | Mullick et al. | |
| 2010/0082280 A1 | 4/2010 | Schneider | |
| 2010/0204562 A1 * | 8/2010 | Gorges et al. ................. | 600/407 |

FOREIGN PATENT DOCUMENTS

| | | |
|---|---|---|
| WO | WO 01/33231 A2 | 5/2001 |
| WO | WO 2004/006770 A2 | 1/2004 |

OTHER PUBLICATIONS

Partial European Search Report dated Apr. 4, 2012 from related European Application No. 11194809.7.

* cited by examiner

*Primary Examiner* — Parikha Mehta
(74) *Attorney, Agent, or Firm* — Louis J. Capezzuto

(57) ABSTRACT

A method, consisting of generating, using a plurality of magnetic transmitters, a magnetic field in a region and introducing a field perturbing element into the region. The method includes characterizing multiple images of each magnetic transmitter in the field perturbing element, and calculating a reaction magnetic field in the region based on the characterized images. The method further includes positioning a probe in the region and measuring a perturbed magnetic field at the probe, and determining a location of the probe in response to the measured perturbed magnetic field and the calculated reaction magnetic field.

31 Claims, 15 Drawing Sheets

COLUMNS 1-2

$$\frac{\sqrt{\frac{3}{\pi}}xz}{2(x^2+y^2+z^2)^{5/2}} \qquad \frac{-2x^2+y^2+z^2}{2\sqrt{6\pi}(x^2+y^2+z^2)^{5/2}}$$

$$\frac{\sqrt{\frac{3}{\pi}}yz}{2(x^2+y^2+z^2)^{5/2}} \qquad -\frac{\sqrt{\frac{3}{2\pi}}xy}{2(x^2+y^2+z^2)^{5/2}}$$

$$-\frac{x^2+y^2-2z^2}{2\sqrt{3\pi}(x^2+y^2+z^2)^{5/2}} \qquad -\frac{\sqrt{\frac{3}{2\pi}}xz}{2(x^2+y^2+z^2)^{5/2}}$$

COLUMN 3

$$-\frac{\sqrt{\frac{3}{2\pi}}xy}{2(x^2+y^2+z^2)^{5/2}}$$

$$\frac{x^2-2y^2+z^2}{2\sqrt{6\pi}(x^2+y^2+z^2)^{5/2}}$$

$$-\frac{\sqrt{\frac{3}{2\pi}}yz}{2(x^2+y^2+z^2)^{5/2}}$$

ELEMENTS OF [$T_{spatial}(x,y,z)$]

FIG. 8A

COLUMNS 4-5

$$-\frac{3x(x^2+y^2-4z^2)}{4\sqrt{5\pi}(x^2+y^2+z^2)^{7/2}} \qquad \frac{\sqrt{\frac{3}{10\pi}}z(-4x^2+y^2+z^2)}{2(x^2+y^2+z^2)^{7/2}}$$

$$-\frac{3y(x^2+y^2-4z^2)}{4\sqrt{5\pi}(x^2+y^2+z^2)^{7/2}} \qquad -\frac{\sqrt{\frac{15}{2\pi}}xyz}{2(x^2+y^2+z^2)^{7/2}}$$

$$\frac{6z^3-9(x^2+y^2)z}{4\sqrt{5\pi}(x^2+y^2+z^2)^{7/2}} \qquad \frac{\sqrt{\frac{3}{10\pi}}x(x^2+y^2-4z^2)}{2(x^2+y^2+z^2)^{7/2}}$$

COLUMN 6

$$-\frac{\sqrt{\frac{3}{10\pi}}y(-4x^2+y^2+z^2)}{2(x^2+y^2+z^2)^{7/2}}$$

$$-\frac{\sqrt{\frac{3}{10\pi}}x(x^2-4y^2+z^2)}{2(x^2+y^2+z^2)^{7/2}}$$

$$\frac{\sqrt{\frac{15}{2\pi}}xyz}{2(x^2+y^2+z^2)^{7/2}}$$

ELEMENTS OF $[T_{spatial}(x,y,z)]$

FIG. 8B

COLUMN 7

$$-\frac{\sqrt{\frac{15}{2\pi}}xyz}{2(x^2+y^2+z^2)^{7/2}}$$

$$\frac{\sqrt{\frac{3}{10\pi}}z(x^2-4y^2+z^2)}{2(x^2+y^2+z^2)^{7/2}}$$

$$\frac{\sqrt{\frac{3}{10\pi}}y(x^2+y^2-4z^2)}{2(x^2+y^2+z^2)^{7/2}}$$

COLUMN 8

$$-\frac{\sqrt{\frac{3}{10\pi}}y(-4x^2+y^2+z^2)}{2(x^2+y^2+z^2)^{7/2}}$$

$$-\frac{\sqrt{\frac{3}{10\pi}}x(x^2-4y^2+z^2)}{2(x^2+y^2+z^2)^{7/2}}$$

$$\frac{\sqrt{\frac{15}{2\pi}}xyz}{2(x^2+y^2+z^2)^{7/2}}$$

ELEMENTS OF [T$_{spatial}$(x,y,z)]

FIG. 8C

COLUMN 9

$$\frac{5xz(4z^2 - 3(x^2 + y^2))}{4\sqrt{7\pi}(x^2 + y^2 + z^2)^{9/2}}$$

$$\frac{5yz(4z^2 - 3(x^2 + y^2))}{4\sqrt{7\pi}(x^2 + y^2 + z^2)^{9/2}}$$

$$\frac{8z^4 - 24(x^2 + y^2)z^2 + 3(x^2 + y^2)^2}{4\sqrt{7\pi}(x^2 + y^2 + z^2)^{9/2}}$$

COLUMN 10

$$\frac{\sqrt{\frac{3}{7\pi}}(4x^4 + 3(y^2 - 9z^2)x^2 - y^4 + 4z^4 + 3y^2z^2)}{8(x^2 + y^2 + z^2)^{9/2}}$$

$$\frac{5\sqrt{\frac{3}{7\pi}}xy(x^2 + y^2 - 6z^2)}{8(x^2 + y^2 + z^2)^{9/2}}$$

$$\frac{5\sqrt{\frac{3}{7\pi}}xz(3(x^2 + y^2) - 4z^2)}{8(x^2 + y^2 + z^2)^{9/2}}$$

ELEMENTS OF [T$_{spatial}$(x,y,z)]

FIG. 8D

COLUMN 11

$$\frac{\sqrt{\frac{15}{14\pi}}xz(5x^2 - 9y^2 - 2z^2)}{4(x^2 + y^2 + z^2)^{9/2}}$$

$$\frac{\sqrt{\frac{15}{14\pi}}yz(9x^2 - 5y^2 + 2z^2)}{4(x^2 + y^2 + z^2)^{9/2}}$$

$$-\frac{\sqrt{\frac{15}{14\pi}}(x-y)(x+y)(x^2 + y^2 - 6z^2)}{4(x^2 + y^2 + z^2)^{9/2}}$$

COLUMN 12

$$\frac{\sqrt{\frac{5}{7\pi}}(-4x^4 + 3(7y^2 + z^2)x^2 - 3y^2(y^2 + z^2))}{8(x^2 + y^2 + z^2)^{9/2}}$$

$$-\frac{\sqrt{\frac{5}{7\pi}}xy(13x^2 - 15y^2 + 6z^2)}{8(x^2 + y^2 + z^2)^{9/2}}$$

$$-\frac{\sqrt{\frac{35}{\pi}}x(x^2 - 3y^2)z}{8(x^2 + y^2 + z^2)^{9/2}}$$

ELEMENTS OF [T$_{spatial}$(x,y,z)]

FIG. 8E

COLUMN 13

$$\frac{5\sqrt{\frac{3}{7\pi}}xy(x^2+y^2-6z^2)}{8(x^2+y^2+z^2)^{9/2}}$$

$$\frac{\sqrt{\frac{3}{7\pi}}(-x^4+3(y^2+z^2)x^2+4y^4+4z^4-27y^2z^2)}{8(x^2+y^2+z^2)^{9/2}}$$

$$\frac{5\sqrt{\frac{3}{7\pi}}yz(3(x^2+y^2)-4z^2)}{8(x^2+y^2+z^2)^{9/2}}$$

COLUMN 14

$$-\frac{\sqrt{\frac{15}{14\pi}}yz(-6x^2+y^2+z^2)}{2(x^2+y^2+z^2)^{9/2}}$$

$$-\frac{\sqrt{\frac{15}{14\pi}}xz(x^2-6y^2+z^2)}{2(x^2+y^2+z^2)^{9/2}}$$

$$-\frac{\sqrt{\frac{15}{14\pi}}xy(x^2+y^2-6z^2)}{2(x^2+y^2+z^2)^{9/2}}$$

ELEMENTS OF [$T_{spatial}(x,y,z)$]

FIG. 8F

COLUMN 15

$$\frac{\sqrt{\frac{5}{7\pi}}xy(-15x^2 + 13y^2 + 6z^2)}{8(x^2 + y^2 + z^2)^{9/2}}$$

$$\frac{\sqrt{\frac{5}{7\pi}}(3x^4 + 3(z^2 - 7y^2)x^2 + 4y^4 - 3y^2z^2)}{8(x^2 + y^2 + z^2)^{9/2}}$$

$$\frac{\sqrt{\frac{35}{\pi}}y(y^2 - 3x^2)z}{8(x^2 + y^2 + z^2)^{9/2}}$$

ELEMENTS OF [T$_{spatial}$(x,y,z)]

FIG. 8G

COMPENSATION FOR MAGNETIC DISTURBANCE DUE TO FLUOROSCOPE

FIELD OF THE INVENTION

The present invention relates generally to sensing the position of an object placed within a living body, and specifically to compensation for magnetic disturbances affecting a sensor of the position.

BACKGROUND OF THE INVENTION

A wide range of medical procedures involve placing objects, such as sensors, tubes, catheters, dispensing devices, and implants, within the body. Real-time imaging methods are often used to assist doctors in visualizing the object and its surroundings during these procedures. Some methods track the objects using the object using magnetic fields. However, disturbances in the magnetic field may create errors in the tracking.

U.S. Pat. No. 6,714,008, to Holmes, et al., whose disclosure is incorporated herein by reference, describes a gradiometric measurement methodology for determining magnetic fields of large objects.

U.S. Patent Application 2004/0034515, to Bar Tal, et al., whose disclosure is incorporated herein by reference, describes a method for estimating position and orientation measurements in electromagnetic systems. The method includes minimizing the difference between a model for the measurements and one or more measurements.

W.I.P.O Patent Publication WO/2004/006770, to Sati, et al., whose disclosure is incorporated herein by reference, describes a method for calibrating medical imaging systems. The method is stated to be able to determine a position of an imaging source and, if applicable, a magnetic field distortion, for each of a plurality of orientations of a C-arm imaging device.

U.S. Patent Application 2005/0107687, to Anderson, whose disclosure is incorporated herein by reference, describes a system for distortion reduction in an electromagnetic tracker. Certain embodiments of the system are stated to include a tracking analysis unit for analyzing a tracking behavior of an instrument and a tracking modification unit for compensating for the tracking behavior of the instrument.

U.S. Patent Application 2007/0055125, to Anderson et al., whose disclosure is incorporated herein by reference, describes an electromagnetic tracking system that includes a field generator and a field sensor arranged to generate and detect, respectively, an electromagnetic field.

U.S. Patent Application 2008/0183064, to Chandonnet et al., whose disclosure is incorporated herein by reference, describes a method for detecting electromagnetic (EM) field distortion. The method includes sampling a sensor assembly positioned within a volume of interest to acquire measurements of EM fields within the volume of interest, and monitoring the measurements to detect EM field distortion within the volume of interest.

U.S. Pat. No. 6,147,480, to Osadchy et al., whose disclosure is incorporated herein by reference, describes a method for tracking an object using energy fields, in the presence of interference due to introduction of an article responsive to the fields, and in the vicinity of the object.

U.S. Pat. No. 5,767,669, to Hansen et al., whose disclosure is incorporated herein by reference, describes a system for determining the position and orientation of remote sensors using pulsed magnetic fields generated from a fixed location. Eddy current distortions are sensed separately and subtracted by the system.

U.S. Pat. No. 7,657,075, to Viswanathan, whose disclosure is incorporated herein by reference, describes a method for determining a transformation of a three-dimensional pre-operative image data set to obtain a registration of the three-dimensional image data with an X-ray imaging system.

U.S. Pat. No. 7,689,019, to Boese et al., whose disclosure is incorporated herein by reference, describes a method and a device for registering 2D projection images of an object relative to a 3D image data record of the same object. A 3D feature contained in an object, which is also identifiable in the 3D images, is symbolically reconstructed.

U.S. Patent Application 2009/0010540, to Mullick et al., whose disclosure is incorporated herein by reference, describes a method for performing image registration. The method comprises obtaining a reference image dataset and a target image dataset and defining an image mask for a region of interest in the reference image dataset.

U.S. Patent Application 2002/0172328, to Dekel, whose disclosure is incorporated herein by reference, describes a method for transforming the spatial coordinates of an instrument into its corresponding X-ray projection image. The method is stated to be based on the registration of the coordinates system of an X-ray beam imaging system with a location device by simultaneously recording the spatial coordinates and the X-ray projection images of a calibration tool.

SUMMARY OF THE INVENTION

An embodiment of the present invention provides a method, including:

generating, using a plurality of magnetic transmitters, a magnetic field in a region;

introducing a field perturbing element into the region;

characterizing multiple images of each magnetic transmitter in the field perturbing element;

calculating a reaction magnetic field in the region based on the characterized images;

positioning a probe in the region and measuring a perturbed magnetic field at the probe; and determining a location of the probe in response to the measured perturbed magnetic field and the calculated reaction magnetic field.

Typically, generating the magnetic field includes measuring the magnetic field absent the field perturbing element, and measuring the magnetic field with the field perturbing element present in the region.

In a disclosed embodiment introducing the field perturbing element into the region includes measuring a location and an orientation of the field perturbing element with respect to axes defined by the magnetic transmitters. Measuring the location and the orientation of the field perturbing element may include calculating the location and the orientation adaptively in response to the reaction magnetic field.

In another disclosed embodiment characterizing the multiple images includes assuming the multiple images are in a predetermined configuration with respect to each other. The predetermined configuration may include a rectangle and the multiple images may include five images located at corners and a center of the rectangle.

In yet another disclosed embodiment calculating the reaction magnetic field includes calculating the field according to a spherical harmonic expansion. Calculating the reaction magnetic field may include performing the spherical harmonic expansion up to order 3.

Alternatively or additionally, calculating the field according to the spherical harmonic expansion may include configuring the expansion as a spatial transfer matrix, and the method may further include determining properties of the field perturbing element as a reaction field matrix, and calculating the reaction magnetic field may be responsive to a product of the spatial transfer matrix and the reaction field matrix.

Typically, positioning the probe includes positioning the probe within a body of a patient.

In one embodiment the field perturbing element includes at least a section of a fluoroscope. The method may include registering fluoroscope-axes, of the fluoroscope, with axes defined by the transmitters. Registering the fluoroscope axes may include forming images of fiducial marks attached to the fluoroscope with cameras fixedly connected to the transmitters. Introducing the field perturbing element may include measuring a location and an orientation of the field perturbing element in response to the images.

There is further provided, according to an embodiment of the present invention, apparatus, including:

a plurality of magnetic transmitters configured to generate a magnetic field in a region;

a field perturbing element introduced into the region; and a processor, which is configured to:

characterize multiple images of each magnetic transmitter in the field perturbing element, calculate a reaction magnetic field in the region based on the characterized images, measure a perturbed magnetic field at a probe positioned in the region, and determine a location of the probe in response to the measured perturbed magnetic field and the calculated reaction magnetic field.

There is further provided, according to an embodiment of the present invention, a method, including:

mounting magnetic transmitters, configured to generate a magnetic field in a patient, on a location pad;

attaching location-pad-cameras with respective fixed orientations to the location pad;

coupling rotatable cameras to the location pad;

attaching fiducial marks to a fluoroscope configured to image the patient;

locating the fluoroscope into different positions; and for each position:

orienting the rotatable cameras into known orientations, and forming respective images of the fiducial marks with the rotatable cameras and the location-pad cameras, and analyzing the respective images to register a location and an orientation of the fluoroscope with an axis of the location pad.

The method may include removing the rotatable cameras from the location pad, and determining the location and orientation of the fluoroscope with respect to the axis of the location pad using only the images of the fiducial marks formed by the location-pad cameras. In one embodiment, attaching the location-pad cameras to the location pad includes attaching a removable jig to the location pad, and aligning the location-pad cameras to the respective fixed orientations by imaging the jig with the cameras.

There is further provided, according to an embodiment of the present invention, apparatus, including:

a location pad;

magnetic transmitters, configured to generate a magnetic field in a patient, which are mounted on the location pad;

location-pad-cameras which are attached with respective fixed orientations to the location pad;

rotatable cameras coupled to the location pad;

a fluoroscope configured to image the patient;

fiducial marks attached to the fluoroscope; and a processor, configured to:

locate the fluoroscope into different positions, and for each position:

orient the rotatable cameras into known orientations, and form respective images of the fiducial marks with the rotatable cameras and the location-pad cameras, and analyze the respective images to register a location and an orientation of the fluoroscope with an axis of the location pad.

The present disclosure will be more fully understood from the following detailed description of the embodiments thereof, taken together with the drawings, in which:

BRIEF DESCRIPTION OF THE DRAWINGS

FIGS. 8A-8G show the elements of a matrix, according to an embodiment of the present invention.

DETAILED DESCRIPTION OF EMBODIMENTS

Overview

Embodiments of the present invention provide a method for compensating for perturbations created in a magnetic field in a region. The perturbations are caused by introduction of a perturbing element, typically a metallic component, into a field generated by magnetic transmitters. In order to compensate for the presence of the perturbing element, a reaction field model used by embodiments of the present invention assumes that each magnetic transmitter creates multiple images of the transmitter in the element. The model assumes that each image generates a respective reaction field, which in total act to perturb the field generated by the transmitters.

Each image may typically be characterized as a combination of multipoles, i.e., dipoles, quadrupoles and/or higher order poles. Characteristics of each image are also dependent, inter alia, on the transmitter field generating the image. The model typically calculates the reaction field from each of the multipolar images by assuming that the field can be represented by a spherical harmonic expansion, and according to characteristics of the images. Typically, the image characteristics are effectively determined by measuring the field from the transmitters in the presence of the perturbing element, as well as without the perturbing element, and the characteristics may be represented in terms of a spatial transfer matrix and a reaction field matrix.

Once the images have been characterized, a probe that is positioned in the region measures the perturbed magnetic field. A location of the probe in the region may then be calculated in response to the measured field and the reaction field calculated as described above.

System Description

Figure 1:
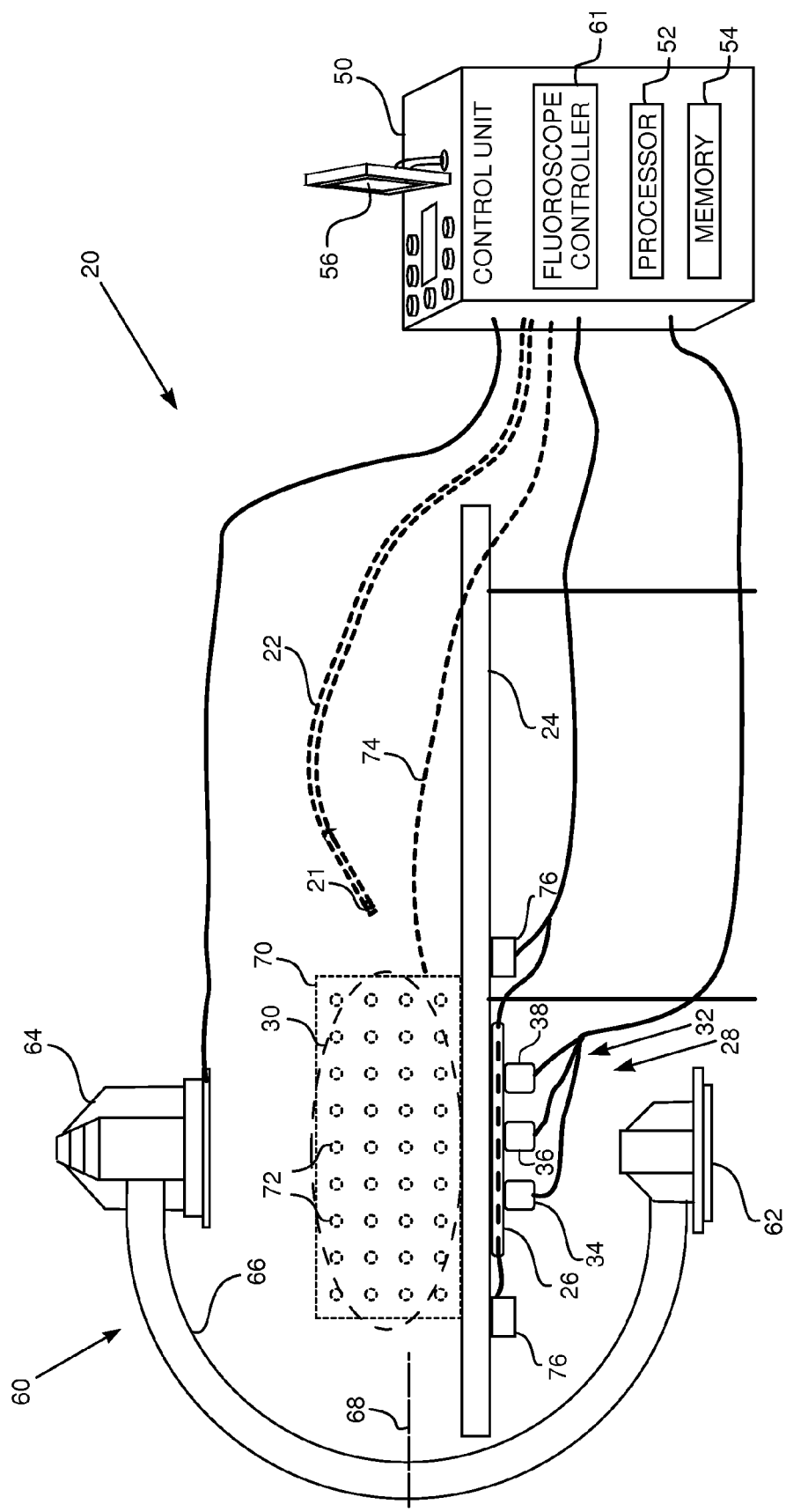
FIG. 1 is a schematic, pictorial illustration of a position sensing system, according to an embodiment of the present invention.
Figure 2:
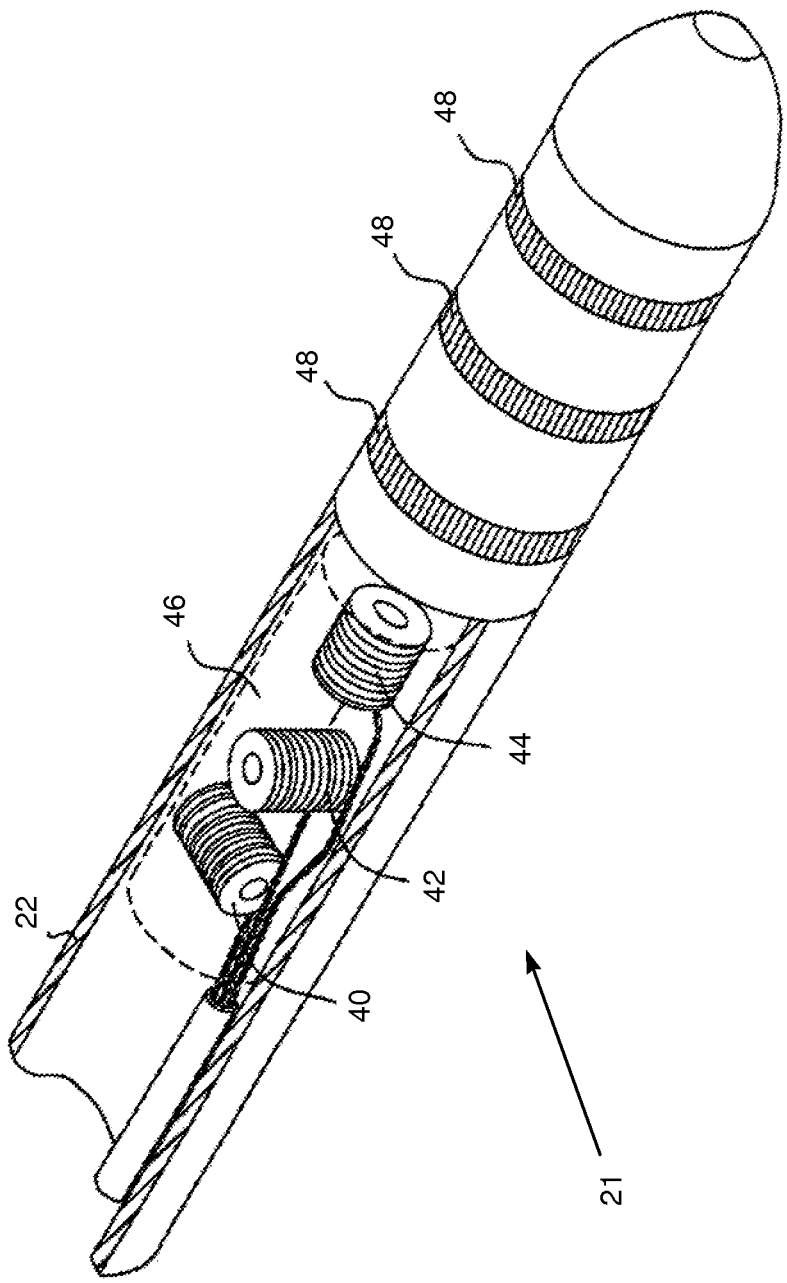
FIG. 2 is a schematic detailed view showing a distal end of a probe, according to an embodiment of the present invention.
Figure 3:
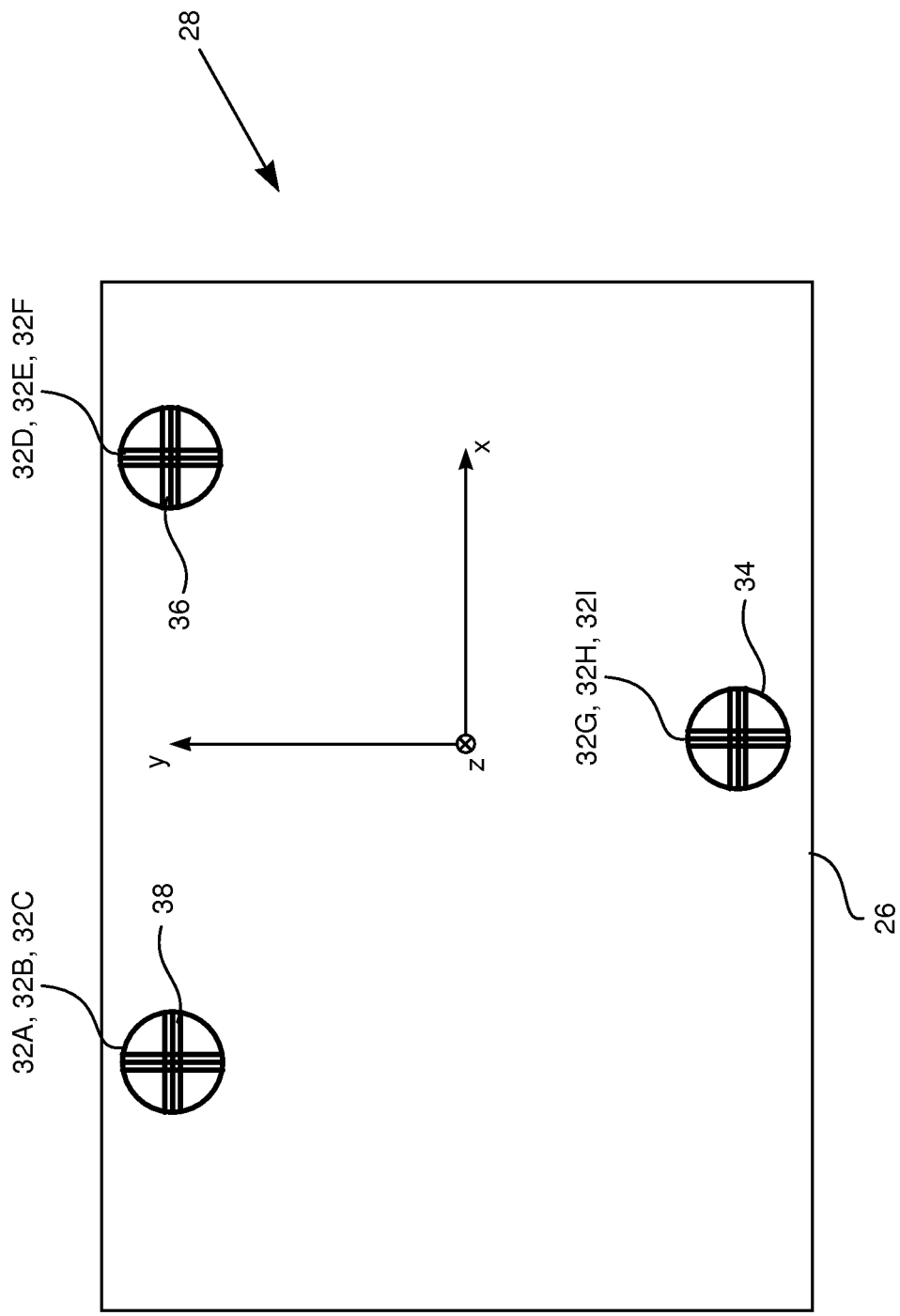
FIG. 3 is a schematic illustration of elements used in the position sensing system, according to an embodiment of the present invention.

Reference is now made to FIG. 1, which is a schematic, pictorial illustration of a position sensing system 20 which is configured to sense the position of a distal end 21 of a catheter probe 22, to FIG. 2, which is a schematic detailed view showing distal end 21, and to FIG. 3, which is a schematic illustration of elements used in system 20, according to embodiments of the present invention. Typically probe 22 is inserted into a body cavity or organ of a patient by a medical professional during an operational phase of system 20, and is not present during a calibration phase of the system. For clarity, probe 22 is shown in FIG. 1 with broken lines. The patient typically lies on an operating table 24 during a procedure performed by the medical professional, who may operate position sensing system 20. For clarity and simplicity, neither the patient nor the medical professional are shown in FIG. 1.

By way of example, in the description hereinbelow probe 22 is assumed to be used in an invasive procedure within a chamber of a heart of the patient. The patient is placed on table 24 in a magnetic field which is generated by positioning, under the patient, a location pad 26 containing an arrangement 28 of generally similar alternating magnetic field transmitter coils 32A, 32B, . . . . The coils are also collectively referred to herein as magnetic field transmitter coils 32. Coils 32 generate their alternating magnetic fields in a region 30, schematically illustrated in FIG. 1 as an ellipse. FIG. 3 illustrates an exemplary arrangement of coils 32.

Typically, and as illustrated in FIG. 3, arrangement 28 comprises transmitter coils 32 formed as three sets of triaxial coils 34, 36, and 38, each set of triaxial coils comprising three coils that are orthogonal to each other. However, arrangements of magnetic transmitter coils 32 other than arrangement 28 are possible, and such arrangements will be evident to those having ordinary skill in the art. U.S. Pat. No. 6,484,118, to Govari, whose disclosure is incorporated herein by reference, describes an arrangement of coils similar to arrangement 28, as well as other arrangements of coils 32 which may be used in system 20.

The description herein assumes that distal end 21 comprises three generally orthogonal coils 40, 42, and 44 as part of an electromagnetic (EM) sensor 46 located at the distal end. (The distal end typically comprises other elements, such as electrodes 48 illustrated in FIG. 2.) The magnetic fields generated by coils 32 produce electrical signals in the coils of sensor 46, according to the fields sensed by the coils. The electrical signals from the coils of sensor 46 are conveyed to a control unit 50, which analyzes the signals so as to determine the coordinates of the position and of the orientation of probe 22. The coordinates are assumed to be referenced to a set of orthogonal xyz axes, illustrated in FIG. 3, which are fixed with respect to location pad 26.

Other arrangements of coils in distal end 21, for detecting the position and orientation of probe 22, are known in the art. One such arrangement uses one coil, which measures projections of fields. Those having ordinary skill in the art will be able to adapt the present description, mutatis mutandis, to account for coil arrangements different from the one exemplified by coils 40, 42, and 44.

Control unit 50 includes a processor 52, typically a computer with appropriate signal processing circuits. The processor uses a memory 54, which typically comprises both volatile and non-volatile data storage devices, wherein data for operating system 20 is stored. The processor is coupled to drive a console which may provide a visual display 56 of the location of probe 22.

System 20 includes a fluoroscope 60, which is operated by a fluoroscope controller 61, and which is able to produce fluoroscopic images of the patient on table 24. Fluoroscope controller 61 is assumed to be a sub-unit of control unit 50. Fluoroscope 60 has a number of sections, comprising a collimated X-ray source 62, also referred to herein as collimator 62, and a detector 64. The collimator and the detector are connected together by another section, a "C-beam" 66, which allows them to be rotated about two axes, a horizontal axis 68, and an axis perpendicular to the plane of the paper through axis 68. The C-beam also allows the collimator and detector to be translated in space, such as in a direction parallel to the horizontal axis. C-beam 66 maintains the collimator and detector in a fixed alignment with each other, and at a constant distance from each other, during rotation of the fluoroscope about axis 68. Typically, the images formed by fluoroscope 60 may be formed with the fluoroscope rotated to any orientation about axis 68, the orientation being selected according to the needs of the patient and the requirements of the professional operating system 20.

Typically, fluoroscope 60 operates to produce its images at substantially the same time as probe 22 is being used. However, metallic components of the fluoroscope which are in proximity to region 30 alter the magnetic fields generated by coils 32 in the region. Without compensation for these alterations, inaccuracies in the measured location of probe 22 are introduced. As described herein, embodiments of the present invention compensate for the alterations in field produced by fluoroscope 60, regardless of the orientation or position of the fluoroscope relative to table 24, so preventing any inaccuracies in the measured location of the probe.

Typically, system 20 includes other elements, which are not shown in the figures for the sake of simplicity, and which are referred to as necessary in the following description. For example, system 20 may include an ECG monitor, coupled to receive signals from one or more body surface electrodes, so as to provide an ECG synchronization signal to control unit 50.

The configuration of FIG. 1 is an example configuration, which is chosen purely for the sake of conceptual clarity. In alternative embodiments, any other suitable configuration can also be used. Typically, processor 52 is programmed in software to carry out the functions described herein. The software may be downloaded to the processor in electronic form, over a network, for example, or it may, alternatively or additionally, be provided and/or stored on non-transitory tangible media, such as magnetic, optical, or electronic memory.

System 20 also comprises apparatus which is able to plot the magnetic fields that are generated by coils 32 in region 30. In one embodiment of the present invention, a mapper 70 is used to plot the magnetic fields, the mapper comprising an array of magnetic field detectors 72 which are fixedly mounted in known positions on solid bases, such as sheets of plastic. Mapper 70 is configured so that it may be positioned on table 24 in a known predetermined position and orientation relative to location pad 26. In one embodiment, mapper 70 comprises 50 detectors. Typically, the detectors are configured in the mapper so that the magnetic field and all its non-negligible gradients are measurable. In an alternative embodiment, the mapper has 78 detectors distributed in a rectangular box having approximate dimensions of height×width×length equal to 150 mm×250 mm×250 mm.

The mapper may be positioned, typically approximately centrally with respect to left and right, and head and foot, using magnetic measurements from detectors 72.

Although in the following description of the operation of system 20 it is assumed that mapper 70 is used to plot magnetic fields, it will be understood that the mapper is an exemplary system for measuring the magnetic fields in region 30, and any other suitable system, such as one or more field detectors that may be moved into known positions, may be used. Such alternative field plotting systems will be apparent to those having ordinary skill in the art, and are assumed to be comprised within the scope of the present invention.

Detectors 72 may comprise any convenient sensors for measuring the magnitude and direction of a magnetic field, such as Hall probes or sensors generally similar to sensor 46. The readings from the detectors are transferred to control unit 50, typically by a cable 74, although any other convenient transfer method may be used, such as wireless transmission.

As described in more detail below, mapper 70 is used in the calibration phase of system 20, so that the mapper and its connecting cable are shown in FIG. 1 with broken lines. The mapper and its cable are removed when system 20 is in its operational phase.

In some embodiments system 20 comprises one or more reference sensors 76 which are generally similar to sensor 46. Sensors 76 provide signals to control unit 50 to enable the unit, as described below, to determine the position and orientation of fluoroscope 60. Typically, sensors 76 are fixed relative to table 24, and may conveniently be located beneath the table. Alternatively, reference sensors 76 may be fixed to fluoroscope 60.

Figure 4:
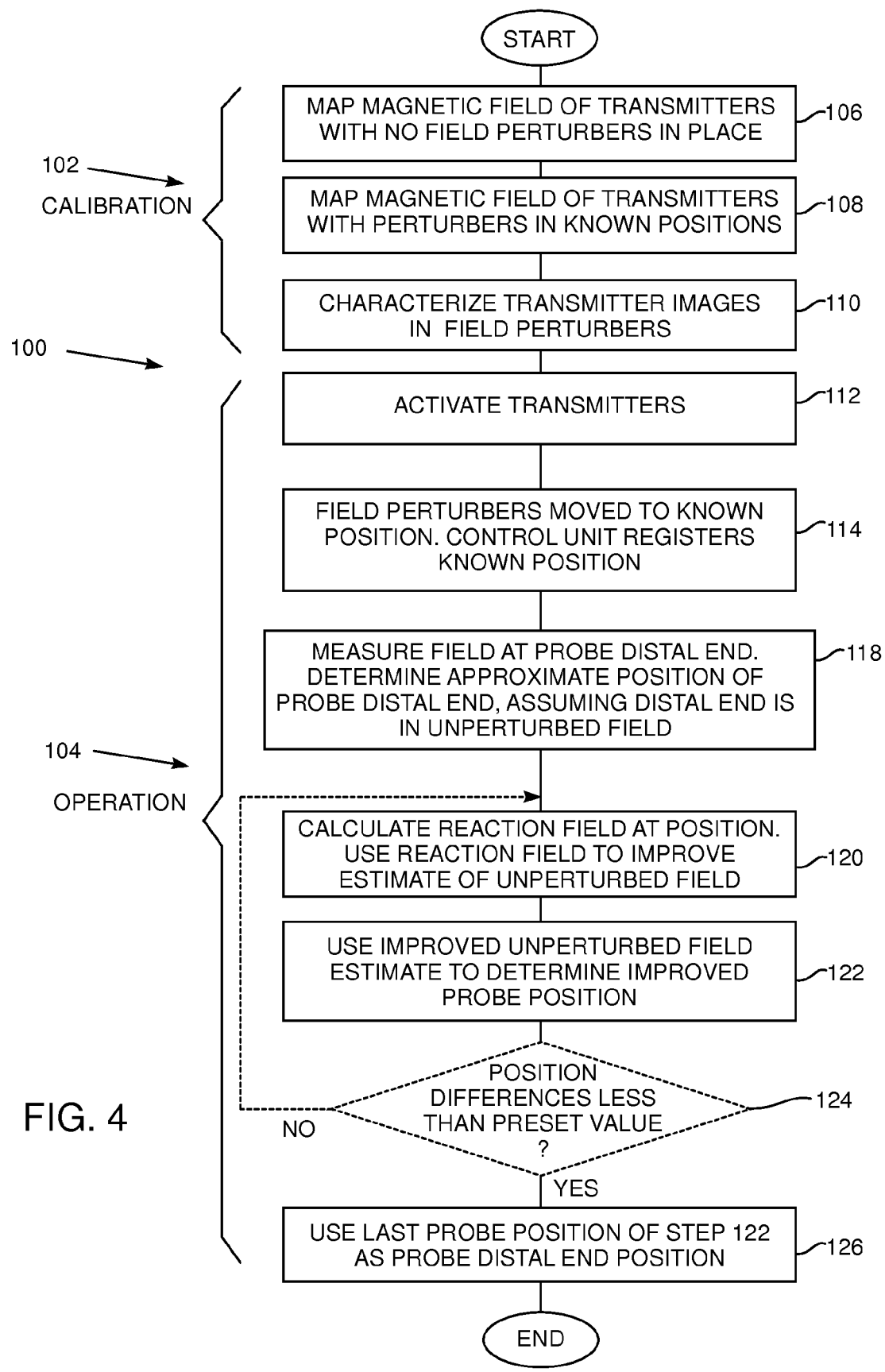
FIG. 4 is a flow chart of a procedure for determining the location of the distal end of the probe, according to an embodiment of the present invention.

Reference is now made to FIG. 4, which is a flow chart 100 of a procedure for determining the location of distal end 21 of probe 22, according to an embodiment of the present invention. Flow chart 100 comprises a first calibration phase 102, followed by a second operational phase 104. The following description of the flow chart also refers to parts of the section headed "Reaction Field Model" below.

In a first mapping step 106 of the calibration phase, all objects, herein termed field perturbers or field perturbing elements, that could perturb the field generated by coils 32 are removed from region 30 and its vicinity. Such objects include fluoroscope 60. Mapper 70 is positioned on table 24 in its predetermined position and orientation relative to location pad 26, and transmitter coils 32 are activated. Control unit 50 operates magnetic field detectors 72 so as to map the unperturbed magnetic field in region 30.

In a second mapping step 108, with mapper 70 remaining in place, fluoroscope 60 is placed into specific locations and orientations (LOs) with respect to the location pad axes, in the vicinity of region 30. Control unit 50 may determine the specific LOs using fluoroscope controller 61. Alternatively, in embodiments comprising reference sensors 76, control unit 50 may use signals from the sensors to determine the LOs, as described below in the section entitled Adaptive Fluoroscope Location. A further alternative optical method for determining the known LOs of the fluoroscope is described below with reference to FIGS. 5, 6A, 6B, and 7.

As described below, fluoroscope 60 is assumed to have two perturbing elements: collimator 62 and detector 64. In order that the characterization described below for step 110 is valid, the different LOs are selected so that they are in two sets: a first set where collimator 62 is far from region 30, so that only detector 64 is the perturbing element, and a second set where detector 64 is far from region 30, so that only collimator 62 is the perturbing element.

For each known LO, control unit 50 operates magnetic field detectors 72 so as to map the perturbed magnetic field in region 30.

In a multipole characterization step 110, the control unit assumes that the perturbation caused by each perturbing element of fluoroscope 60 is due to reaction fields generated by magnetic image sources in the respective element. The analysis performed in step 110 is described in more detail below in the section entitled Reaction Field Model. The magnetic sources may be considered to be images of transmitter coils 32 in the perturbing elements, i.e., in the two elements: collimator 62 and detector 64. Those having ordinary skill in the art will be able to adapt the description if fluoroscope 60 has different numbers of elements, or for the case of other field perturbers.

Theoretically, if a field perturber is a perfectly conducting sphere and the transmitter is a dipole with its moment directed towards the center of the sphere, then the image of the transmitter generated by the sphere is a single dipole. To allow for the differences from such a theoretical model, which include, inter alia, the transmitter not being a perfect dipole, and the perturber not being a perfectly conducting sphere, embodiments of the present invention assume that within each perturbing element of the fluoroscope a single transmitter coil 32 generates two or more multipole magnetic source images of the coil.

Each multipole is assumed to generate a respective reaction field, and a multipole may comprise dipole, quadrupole and/or higher order poles. To take account of the possibility of the image sources of the reaction field having components other than dipoles, rather than analyzing the data using discrete poles, control unit 50 uses spherical harmonic analysis. As explained in the section Reaction Field Model, and by way of example, herein each coil 32 is assumed to generate five multipole images in collimator 62, and five multipole images in detector 64. The locations of the images act as expansion points for the spherical harmonic functions assumed to describe the reaction fields. Those with ordinary skill in the art will be able to adjust the present description for other numbers of images in the collimator and/or the detector.

At the conclusion of step 110, which is typically the conclusion of the calibration phase, the control unit has characterized all the multiple image sources of each perturbing element. For each perturbing element, the characterization includes locations of the image sources in the perturber, and determining the elements of a reaction field matrix $[T_{reaction}]$ generated by the image sources of each perturbing element. For the exemplary embodiment considered here, wherein collimator 62 and detector 64 are the perturbing elements, respective matrices $[T_{reaction}]_{collimator}$ and $[T_{reaction}]_{detector}$ are determined.

In one embodiment the detector has an outer rectangular frame having dimensions of 38 cm×48 cm. The five image sources for the detector are assumed to be located approximately 10 cm from the rectangle corners and at the center of the rectangle, and approximately 10 cm beneath the surface of the detector. The outside of the collimator has similar rectangular dimensions, and the five image sources of the collimator are disposed in a similar manner to those of the detector.

In the operational phase, the unit uses matrices $[T_{reaction}]_{collimator}$ and $[T_{reaction}]_{detector}$ to calculate the reaction field generated by the image sources.

In a first operational phase step 112, the control unit activates transmitter coils 32, in the event that they have been deactivated after step 110.

In a perturbation step 114, fluoroscope 60 is moved into a known LO, i.e., the detector is in a known LO and the collimator is also in a known LO, in the vicinity of region 30, and control unit 50 registers the known LOs. The known LOs may be provided to control unit 50 by one of the methods described above for the calibration process.

In an initial position determining step 118, the control unit measures signals generated from the sensors in distal end 21 of probe 22. The control unit, as a first approximation, assumes that the field determined from the signals is an unperturbed field. Using the results from first mapping step 106, the control unit determines an approximate position of the distal end.

In a field correction step 120, control unit 50 calculates the reaction field, at the position determined in the previous step, using equation (7). The control unit subtracts the reaction field from the measured field to generate an improved estimate of the unperturbed field at the position.

In an improved position determination step 122, the control unit uses the unperturbed field value and the value of the field determined in step 120 to make an improved determination of the position of the distal end.

In an optional comparison step 124, the control unit checks if the difference between the last position and the penultimate position, determined in step 122 is less than a preset value, which is typically approximately 0.1 mm. If the difference is greater than or equal to the preset value, the control unit returns to step 122. If the difference is less than the preset value, the control unit continues to a final step 126.

It will be understood that steps 120-124 describe an optional iterative loop wherein the control unit performs an increasingly exact determination of the position of the distal end, while also performing an increasingly exact determination of the unperturbed field at the position.

In some embodiments, a loop generally similar to that defined by steps 120 and 124, but not including step 122, is performed on temporally sequential measurements. In this case the reaction field correction is applied to the next measurement in time for each sensor. In one such embodiment, where the measurements are calculated every 16 ms, the inventors have found that for a stationary sensor, three or fewer iterations are required to provide a true value of the sensor's position.

In final step 126, the control unit uses the last determination of the position found in step 122 as the position of the distal end.

Figure 5:
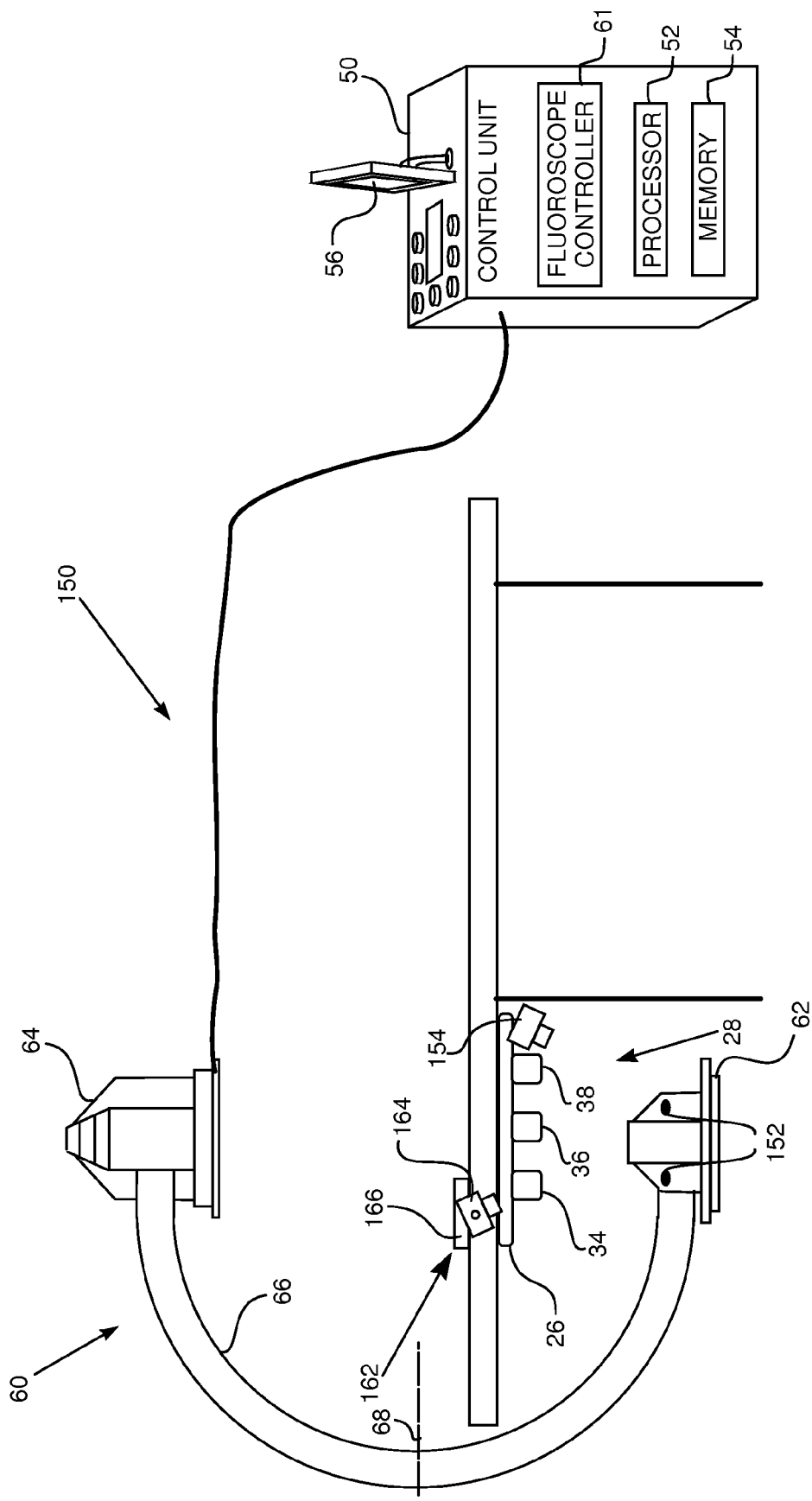
FIG. 5 is a schematic, pictorial illustration of an alternative position sensing system, according to an embodiment of the present invention.
Figure 6A:
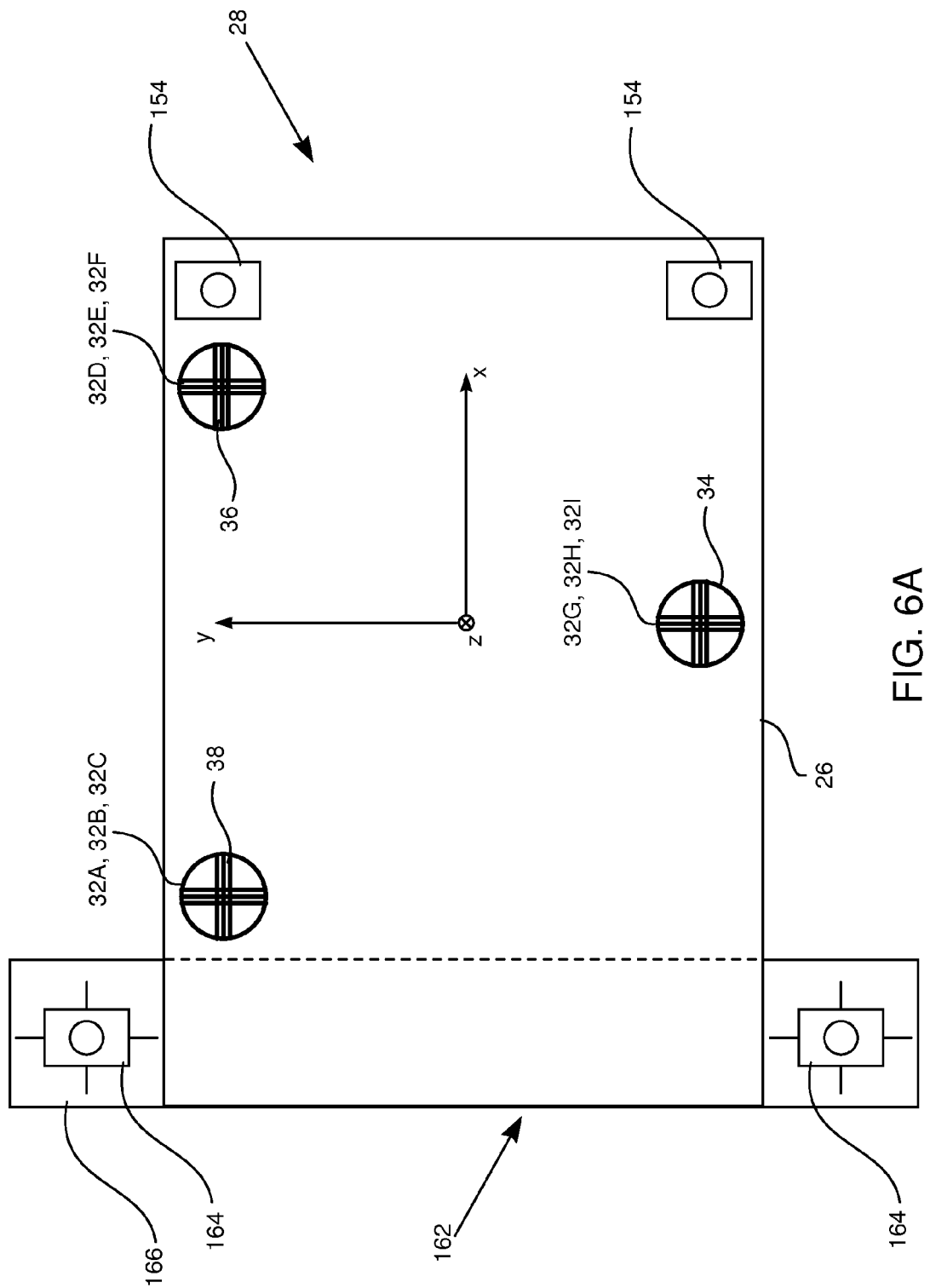
FIGS. 6A and 6B are schematic diagrams of portions of the alternative position sensing system, and of elements used in calibration of the system, according to an embodiment of the present invention.
Figure 6B:
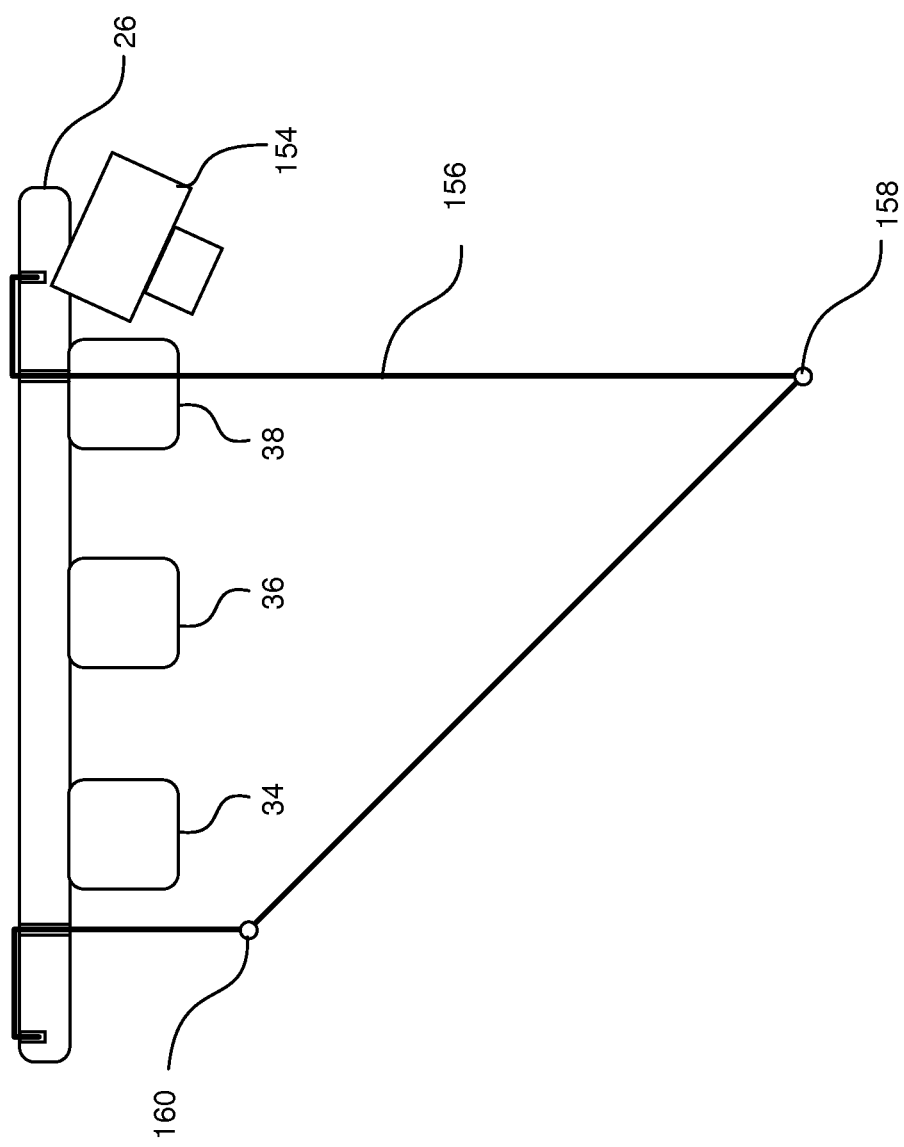

FIG. 5 is a schematic, pictorial illustration of an alternative position sensing system 150, according to an embodiment of the present invention. FIGS. 6A and 6B are schematic diagrams of portions of system 150, and of elements used in calibration of the system, according to an embodiment of the present invention. Apart from the differences described below, the operation of system 150 is generally similar to that of system 20 (FIGS. 1-4), and elements indicated by the same reference numerals in both systems 20 and 150 are generally similar in construction and in operation. For clarity and simplicity, some elements of system 150, that are present in system 20 and are illustrated in FIG. 1, are not shown in FIG. 5.

In system 150, one or more fiducial marks 152 are fixed to an element of fluoroscope 60. Herein, by way of example, two marks 152 are assumed to be attached to collimator 62. In addition, two or more cameras 154 are fixedly attached to location pad 26. Cameras 154 are under control of control unit 50, so that processor 52 is able to receive and process images generated by the cameras. The cameras are fixed to location pad 26 with locations and orientations so that the images they form include images of fiducial marks 152.

As described in more detail below with reference to the flow chart of FIG. 7, control unit 50 uses the camera images of fiducial marks 152 to determine the location and orientation of fluoroscope 60, including its collimator 62 and detector 64, with respect to location pad 26. In order to perform this determination, the locations of the cameras are registered with respect to the location pad. The registration of the cameras with the location pad, and the determination of the relationship of the fiducial mark images with the location and orientation of the fluoroscope, are realized by control unit 50 according to the flow chart of FIG. 7.

The registration may be accomplished using a removable prebuilt calibration jig 156 fitted into a known position in the location pad. In some embodiments jig 156 is collapsible, being hinged at hinges 158 and 160. By making jig 156 collapsible, a field engineer may easily and efficiently retrofit the jig into location pad in an existing position sensing system 20, as is illustrated in FIG. 6B. Images from elements of jig 156 are used to align cameras 154 in the location pad, and to correct for any optical errors that may be introduced by the cameras.

Control unit 50 may determine the relationship of the fiducial mark images with the location and orientation of the fluoroscope using a fluoro calibration system (FCS) 162, illustrated in FIGS. 5 and 6A. FCS 162 comprises a second pair of cameras 164 which can transmit their images to the control unit. The cameras are mounted on a support 166, and each camera is capable of being independently panned and tilted according to commands received from control unit 50.

Figure 7:
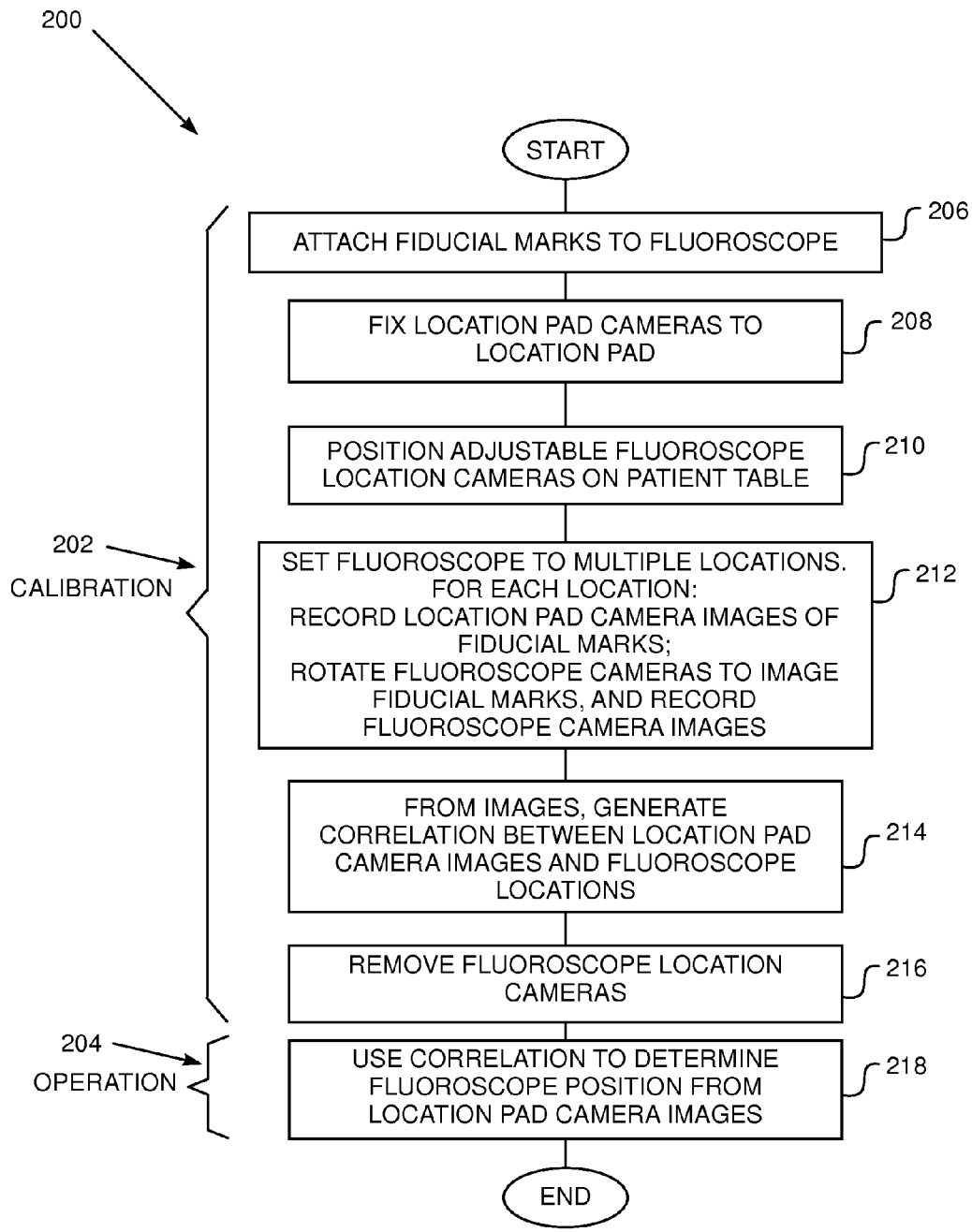
FIG. 7 is a flow chart of steps performed by a control unit in operating the alternative position sensing system, according to an embodiment of the present invention.

FIG. 7 is a flow chart 200 of steps performed by control unit 50 in operating system 150, according to an embodiment of the present invention. Flow chart 200 is divided into a calibration phase 202 and an operational phase 204.

In a first step 206 of the calibration phase, fiducial marks 152 are affixed to fluoroscope 60. The fiducial marks are positioned so as to be in the field of view of cameras 154 when the cameras have been connected, as described below, to location pad 26. Typically, the element of the fluoroscope to which the marks are affixed is selected so that the marks are within the fields of view of at least one of cameras 154 for substantially all the operational positions and orientations of the fluoroscope. Herein, by way of example, the fiducial marks are assumed to be fixed to the collimator. In some embodiments, more than two cameras 154 are used in system 150 so that fiducial marks 152 are within the fields of view of at least one of the cameras for all locations and orientations of the fluoroscope.

In a camera installation step 208, cameras 154 are fixedly attached to location pad 26 so that the cameras are in known locations and have known orientations. In some embodiments the cameras are aligned to their known locations and orientations, after attachment, using jig 156, which acts as a calibration object for the cameras. The images of the jig formed by each of the cameras enable the cameras to be correctly aligned, as well as providing data enabling control unit 50 to correct for imperfections in the imaging of the cameras. Alternatively, any other convenient method for fixing cameras 154 in known locations and orientations with respect to the location pad, and for correcting imperfections in the images of the cameras, may be used.

In a setup step 210, FCS 162 is fixedly positioned in a known location relative to location pad 26. The positioning of FCS 162 may be by attaching support 166 of the FCS to table 24 (as illustrated in FIG. 5), or to any other convenient object, such as location pad 26 itself. FCS 162 is positioned so that cameras 164, mounted on support 166, are able to be rotated by the control unit so that they are always enable to image fiducial marks 152.

In a data measurement step 212, fluoroscope 60 is moved into multiple different positions, i.e., multiple different locations and orientations, using fluoroscope controller 61. In each different position, control unit 50 transmits signals to cameras 164 so that the cameras are at known pan and tilt angles. Control unit 50 causes the cameras to pan and/or tilt so that each camera 164 images fiducial marks 152. Control unit 50 records the pan and tilt angles of each camera (the control unit is aware of the orientation of each camera 164 since it sent the pan and tilt signals), as well as the images of the fiducial marks formed by each camera.

In addition, at each different position of the fluoroscope, control unit 50 records the images of the fiducial marks generated by each camera 154.

In a correlation step 214, control unit 50 generates a correlation between the fiducial mark images of cameras 164 and of cameras 154. The correlation allows the control unit to register the axes of the two systems, i.e., the axis of the fluoroscope and the axis of the location pad.

Once the registration has been performed, in a last step 216 of the calibration phase, FCS 162, including its cameras 164, is removed.

In an operation step 218 of the operational phase, cameras 154 are activated. In the present example, where the fiducial marks are attached to the collimator, the control unit receives fiducial mark images from the cameras, and analyzes the images, using the correlation determined in step 214, to determine the location and orientation of the collimator with respect to the location pad. Since the collimator and detector of fluoroscope 60 are in a fixed physical relationship to each other, the location and orientation of the collimator enables the control unit to know the location and orientation of the detector, up to the distance between them. This missing value is determined typically by using an optimization technique, similar to the Adaptive Fluoroscope Location method described below.

Flow chart 200 has been described with reference to determining the location and orientation of a fluoroscope with respect to the location pad. It will be understood that the steps of the flow chart may be implemented, mutatis mutandis, to determine the location and orientation of another object, typically one which may interfere with the transmitters of the location pad, which is positioned and moves in the vicinity of the location pad. All such implementations are assumed to within the scope of the present invention.

Reaction Field Model

The reaction field model of embodiments of the present invention assumes that the magnetic reaction field, caused by a magnetic perturbing element placed in a source magnetic field, is generated by a plurality of point sources in the element. The source magnetic field may be generated by any number of field transmitters. The point sources may be considered to be images in the perturbing element of a field transmitter.

The description of the model, as related to embodiments of the present invention, makes the following assumptions for simplicity:

Perturbing elements. Fluoroscope 60 comprises collimator 62 and detector 64 connected by C-beam 66. The inventors have found that good results for the reaction field generated by the fluoroscope are obtained if only the detector and collimator are assumed to be perturbing elements, so that in the analysis below only two such elements are assumed. However, the same type of analysis may be applied for other perturbing elements, so that the scope of the present invention includes any number of such elements.

Number of and type of transmitters. To correspond with the three triaxial coils of arrangement 28, there are assumed to be nine magnetic field transmitters. Each of the transmitters is approximately dipolar. However, in general there is no restriction on the number or arrangement of the field transmitters.

Point sources in each perturbing element. By way of example, a given transmitter is assumed to generate as images in each perturbing element five point sources, also herein termed expansion points (since the spherical harmonics referred to below expand from these points). In other embodiments, other numbers of image point sources per transmitter may be assumed, and the number of sources for different perturbing elements does not need to be equal. In embodiments of the present invention the five point sources corresponding to different transmitters are assumed to be congruent with each other. In addition, the five point sources are assumed to be at the center, and at the corners, of a rectangle.

Spherical harmonics. Each point source may be considered to be composed of dipoles, quadrupoles, and/or poles of higher order. Rather than analyzing the separate components, the model assumes that the field from each point source may be represented by a spherical harmonic expansion. The inventors have found that expanding to order 3 gives good results, but it will be appreciated that the scope of the present invention includes expanding to lower or higher orders.

Position Measurements. For simplicity, all positions are assumed to be measured relative to a single set of axes. By way of example, the single set of axes is assumed to be based on detector 64, having its origin at the central image point source of the detector, with x and y axes defined by the sides of the rectangle of the point sources in the detector.

One Transmitter

We first consider one transmitter, and one expansion point formed by the transmitter in a perturbing element, assumed herein, except where otherwise stated, to be detector 64. Assuming for simplicity that the one expansion point is at the origin (0,0,0) of a set of (x,y,z) coordinates based on the detector, an expression for the magnetic reaction field (expressed as a 3 element column vector) at a position (x,y,z) from the origin is:

$$\begin{bmatrix} B_x(x, y, z) \\ B_y(x, y, z) \\ B_z(x, y, z) \end{bmatrix} = [T_{spatial}(x, y, z)] \cdot [C_0] \quad (1)$$

where $$\begin{bmatrix} B_x(x, y, z) \\ B_y(x, y, z) \\ B_z(x, y, z) \end{bmatrix}$$

is the reaction field expressed as a column vector, $[C_0]$ is a 15 element column vector, based on the spherical harmonic terms of orders 1-3, expanded about the origin (an expression for an expanded version of $[C]$ is given below), and $[T_{spatial}(x,y,z)]$ is a 3×15 spatial transfer matrix derived from the spherical harmonic terms of $[C_0]$.

FIGS. 8A-8G show each of the elements of $[T_{spatial}(x,y,z)]$ according to an embodiment of the present invention.

For five expansion points $(0,0,0)$, $(x_1,y_1,z_1)$, $(x_2,y_2,z_2)$, $(x_3,y_3,z_3)$, $(x_4,y_4,z_4)$, equation (1) becomes:

$$\begin{bmatrix} B_x(x,y,z) \\ B_y(x,y,z) \\ B_z(x,y,z) \end{bmatrix} = [T_{spatial}(x,y,z)(5)] \cdot [C_5] \quad (2)$$

where $[T_{spatial}(x,y,z)(5)]$ is a 3×75 spatial transfer matrix, and $[C_5]$ is a 75 element column vector.

$[T_{spatial}(x,y,z)(5)]$ is formed by concatenating four $[T_{spatial}]$ matrices, each offset from the origin by the coordinates of their respective displacements, with $[T_{spatial}(x,y,z)]$. I.e., $$[T_{spatial}(x,y,z)(5)] \equiv [T_{spatial}(x,y,z) \ldots T_{spatial}(x-x_4,y-y_4,z-z_4)] \quad (3)$$

$[C_5]$ is formed by stacking 5 column vectors, each based on spherical harmonic terms expanded about a respective expansion point. I.e., $$[C_5] \equiv \begin{bmatrix} C_0 \\ C_1 \\ C_2 \\ C_3 \\ C_4 \end{bmatrix} \quad (4)$$

Field from One Transmitter

The field from any given transmitter at any point in region 30 may be calculated from the calibration performed during the manufacturing process of the location pad. For characterizing the transmitter we consider a number of points in the region of detector 64. The inventors have found 17 points to be sufficient, but any other convenient number may be used. The field at the points may be represented by a 51 element column vector $[B_{satellite}]$ of the unperturbed field where $$[B_{satellite}] \equiv \begin{bmatrix} B_x^1 \\ B_y^1 \\ B_z^1 \\ \vdots \\ B_x^{17} \\ B_y^{17} \\ B_z^{17} \end{bmatrix} \quad (5)$$

$[C_5]$ is assumed to be dependent on $[B_{satellite}]$ according to the following equation:

$$[C_5] = [T_{reaction}] \cdot [B_{satellite}] \quad (6)$$

where $[T_{reaction}]$ is a 75×51 reaction matrix with elements representing the reaction properties of the detector.

General Case

Using the above derivations, an expression for the detector reaction magnetic field at a point $(x,y,z)$ may be written as equation (7) below. The expression assumes there are nine transmitters and five expansion points in the detector.

$$[Breac(x,y,z)] = [T_{spatial}(x,y,z)(5)] \cdot [T_{reaction}] \cdot [B_{satellite}(9)] \quad (7)$$

where $[Breac(x,y,z)]$ is a 3×9 reaction field matrix having 9 columns, each similar to the column of the reaction field vector of equation (1), $$[Breac(x,y,z)] \equiv \begin{bmatrix} B_x^1 & & B_x^9 \\ B_y^1 & \ldots & B_y^9 \\ B_z^1 & & B_z^9 \end{bmatrix} \quad (8)$$

$[B_{satellite}(9)]$ is a 51×9 matrix of the unperturbed field, having columns similar to vector $[B_{satellite}]$ (equation (5)), $$[B_{satellite}(9)] \equiv \begin{bmatrix} B_x^{1,1} & & B_x^{1,9} \\ \vdots & \ldots & \vdots \\ B_z^{17,1} & & B_z^{17,9} \end{bmatrix} \quad (9)$$

and $[T_{spatial}(x,y,z)(5)]$ and $[T_{reaction}]$ have the same dimensionality as for equations (2) and (6), but elements corresponding to the requirements of equation (7).

It will be appreciated that the product $[T_{spatial}(x,y,z)(5)] \cdot [T_{reaction}]$ effectively characterizes the five images formed in the detector.

Equation (7) may be used in both the calibration phase and in the operational phase of system 20, as described below.

In some embodiments, rather than using equation (7) as is, the equation is adapted by dividing $[Breac(x,y,z)]$ and $[T_{spatial}(x,y,z)(5)]$ by $\|B(x,y,z)\|$, where $B(x,y,z)$ is the unperturbed field from the transmitters at $(x,y,z)$. The inventors have found that such adaptation may give greater weight to locations where the transmitter field is weak, and may compensate for errors in measurement of this field.

For simplicity, the description herein assumes that equation (7) is used as is, and those of ordinary skill in the art will be able to alter the description, mutatis mutandis, for embodiments implementing the adaptation to equation (7) described above.

Calibration Phase

In the calibration phase, equation (7) is used to find values of $[T_{reaction}]$.

For a specific position $(x,y,z)$ the elements of $[Breac(x,y,z)]$ may be found by finding the difference between the field with detector 64 in a position where it perturbs the field, and with the detector positioned so as not to perturb the field.

The elements of $[T_{spatial}(5)(x,y,z)]$ may be found from the equations shown in FIG. 8, assuming the positions of the expansion points (referred to with reference to equation (2)) are used, as appropriate, in the equations.

Thus, in equation (7), all terms except $[T_{reaction}]$ are known.

$[T_{reaction}]$ may be found by manipulating equation (7), by methods which will be familiar to those having ordinary skill in the art. One such method for finding $[T_{reaction}]$ vectorizes $[Breac(x,y,z)]$ and $[T_{reaction}]$, and applies the Kronecker product, $\otimes$, to produce a reformed equation:

$$\text{vec}[Breac(x,y,z)] = [B_{satellite}(9)]^T \otimes [T_{spatial}(5)(x,y,z)] \cdot \text{vec}[T_{reaction}]. \quad (10)$$

where the superscript T indicates the transpose.

$\text{vec}[T_{reaction}]$ is found by multiplying both sides of equation (10) by $([B_{satellite}(9)]^T \otimes [T_{spatial}(5)(x,y,z)])^+$ (the pseudo-inverse of $([B_{satellite}(9)]^T \otimes [T_{spatial}(5)(x,y,z)])$. $[T_{reaction}]$ is generated by breaking $\text{vec}[T_{reaction}]$ into appropriate column lengths.

Such a method finds $[T_{reaction}]$ for one value of $(x,y,z)$ and for the detector (and consequently the expansion points) in a specific position.

In the calibration phase mapper 70 is assumed to make measurements on N values of (x,y,z), using N sensors. For N points $(x_1,y_1,z_1), \ldots, (x_N,y_N,z_N)$ equation (10) may be rewritten, by stacking the matrices of the equation:

$$\begin{bmatrix} vec(Breac(x_1, y_1, z_1)) \\ \vdots \\ vec(Breac(x_N, y_N, z_N)) \end{bmatrix} = \begin{bmatrix} [B_s]^T \otimes [T_s(x_1, y_1, z_1)] \\ \vdots \\ [B_s]^T \otimes [T_s(x_1, y_1, z_1)] \end{bmatrix} \cdot vec[T_{reaction}] \quad (11)$$

Equation (11) is for one detector position, and may be rewritten:

$$[vec[B_{pos1}]] = [B_S^T \otimes T_S]_{pos1} \cdot vec[T_{reaction}] \quad (12)$$

Assuming that in the calibration phase the detector is placed into M positions, equation (12) may be adapted, by further stacking of matrices, to form equation (13):

$$\begin{bmatrix} [vec[B_{pos1}]] \\ \vdots \\ [vec[B_{posM}]] \end{bmatrix} = \begin{bmatrix} [B_S^T \otimes T_S]_{pos1} \\ \vdots \\ [B_S^T \otimes T_S]_{posM} \end{bmatrix} \cdot vec[T_{reaction}] \quad (13)$$

As for the method described above for solving equation (10), the solution for $[T_{reaction}]$ in equation (13) may be found by multiplying both sides of the equation by the pseudo-inverse of $$\begin{bmatrix} [B_S^T \otimes T_S]_{pos1} \\ \vdots \\ [B_S^T \otimes T_S]_{posM} \end{bmatrix}.$$

In an embodiment where N=50 and M=30, matrix $$\begin{bmatrix} [B_S^T \otimes T_S]_{pos1} \\ \vdots \\ [B_S^T \otimes T_S]_{posM} \end{bmatrix}$$

has approximate dimensions of 40,000×4,000. The pseudo-inverse, as is known in the art, may be found using singular value decomposition. In one embodiment, the number of singular values in the pseudo-inverse is minimized by finding a point at which the quality of the solution, i.e., how well the solution corrects for the perturbation, begins to degrade. Typically, values up to approximately $10^{-6}$ are used.

The calibration phase is typically performed to find a $[T_{reaction}]$ for each perturbing element. Thus, for fluoroscope 60, wherein collimator 62 and detector 64 are assumed the only perturbing elements, a matrix $[T_{reaction}]_{collimator}$ and a matrix $[T_{reaction}]_{detector}$ are found. To find $[T_{reaction}]_{collimator}$, typically table 24 is lowered while the fluoroscope positions are changed, so that the effect of the detector is negligible. Similarly, to find $[T_{reaction}]_{detector}$, typically table 24 is raised while the fluoroscope positions are changed.

Operational Phase

In the operational phase the values of $[T_{reaction}]$ determined in the calibration phase are substituted into equation (7) to find the value of $[Breac(x,y,z)]$. If there is more than one perturbing element, then the reaction field is assumed to be the linear superposition of the respective values of $[Breac(x,y,z)]$ from each element.

Adaptive Fluoroscope Location

Referring back to FIG. 1, embodiments of the present invention provide a method for adaptively locating fluoroscope 60 with respect to location pad 26. The method assumes that a preliminary registration of the fluoroscope frame of reference has been made with the location pad frame of reference, by any convenient process. Such a process typically images an object on table 24 using the fluoroscope, finds distances to the object from coils 32 of the location pad, and performs the registration by comparing the images with the distances. The process is typically applied for a number of different positions of the fluoroscope, and uses known parameters of the fluoroscope such as the collimator to detector distance, and the orientation of the fluoroscope as it images the object. The preliminary registration is typically performed at the beginning of a clinical procedure being performed on the patient in system 20.

During the procedure three patch electrodes are typically placed on the chest of the patient, and it is herein assumed that each patch comprises a sensor similar to sensor 76. While the patch sensors typically vary in position with respect to the location pad, these positions may be estimated from the fields they detect. All five sensors (each having three coils) are subject to the nine transmitted fields from coils 32, as well as to the image fields from the collimator and the detector, so that at any time there are 135 independently valued measured signals, herein termed "Meas," from the sensors that are input to processor 52. It will be understood that this number of signals provides a highly redundant set of values in terms of the number of degrees of freedom required to completely describe the location and orientation of the fluoroscope and its components. Furthermore, the unperturbed fields measured at sensors 76 allow direct measures of the reaction fields at the sensors.

Processor 52 is thus able to use signals Meas to calculate the location and orientation of the fluoroscope, as well as the positions of detector 64 and collimator 62. The processor calculates the following cost function:

$$C = \frac{\sum_{sensors} \|Meas - M(\vec{r}_{sensor}, \vec{o}_{sensor}, \varphi_{fluoro}, \theta_{fluoro}, d_{det}, d_{col})\|}{\sum_{sensors} \|Meas\|} \quad (14)$$

where M is a sum of fields generated by location pad 26 and the reaction field model described above, $\vec{r}_{sensor}$ is the displacement of a sensor, $\vec{O}_{sensor}$ is the orientation of a sensor, $\varphi_{fluoro}$ is the elevation of fluoroscope 60, $\theta_{fluoro}$ is the azimuth of fluoroscope 60, $d_{det}$ is the distance of detector 64, and $d_{col}$ is the distance of collimator 62, and where all the above variables are calculated with respect to the location pad axes and origin.

In order to calculate the location and orientation of the fluoroscope, and its components, the processor optimizes cost function C. The optimization typically involves calculating first and higher order derivatives of C, and may use any method for optimization known in the art.

While the description above has referred to elements of a fluoroscope that are magnetic field perturbing elements, it will be understood that the scope of the present invention includes other perturbing elements. For example, probe 22 may comprise metallic components that perturb the magnetic field generated by arrangement 28, and the perturbation produced by these components may be compensated for in a substantially similar manner as is described herein for the fluoroscope elements. Such metallic components may include, but are not limited to, operating tables or parts thereof.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A method, comprising:
    generating, using a plurality of magnetic transmitters, a first magnetic field in a region;
    measuring the first magnetic field without a field perturbing element within the region;
    introducing a field perturbing element into the region;
    characterizing multiple images of each magnetic transmitter in the field perturbing element;
    calculating a reaction magnetic field in the region based on the characterized images;
    positioning a probe in the region and measuring a perturbed magnetic field at the probe;
    determining an approximate location of the probe using the perturbed magnetic field;
    calculating a second reaction field at the approximate location of the probe using the first reaction magnetic field;
    subtracting the second reaction field from the first magnetic field to determine a second magnetic field; and
    determining a corrected location of the probe in response to the first magnetic field and the second magnetic field.

2. The method according to claim 1, wherein introducing the field perturbing element into the region comprises measuring a location and an orientation of the field perturbing element with respect to axes defined by the magnetic transmitters.

3. The method according to claim 2, wherein measuring the location and the orientation of the field perturbing element comprises calculating the location and the orientation adaptively in response to the reaction magnetic field using an optimized cost function.

4. The method according to claim 1, wherein characterizing the multiple images comprises assuming the multiple images are in a predetermined configuration with respect to each other.

5. The method according to claim 4, wherein the predetermined configuration comprises a rectangle and wherein the multiple images comprise five images located at corners and a center of the rectangle.

6. The method according to claim 1, wherein calculating the reaction magnetic field comprises calculating the field according to a spherical harmonic expansion.

7. The method according to claim 6, wherein calculating the reaction magnetic field comprises performing the spherical harmonic expansion up to order 3.

8. The method according to claim 6, wherein calculating the field according to the spherical harmonic expansion comprises configuring the expansion as a spatial transfer matrix, the method further comprising determining properties of the field perturbing element as a reaction field matrix, and wherein calculating the reaction magnetic field is responsive to a product of the spatial transfer matrix and the reaction field matrix.

9. The method according to claim 1, wherein positioning the probe comprises positioning the probe within a body of a patient.

10. The method according to claim 1, wherein the field perturbing element comprises at least a section of a fluoroscope.

11. The method according to claim 10, and comprising registering fluoroscope-axes, of the fluoroscope, with axes defined by the transmitters.

12. The method according to claim 11, wherein registering the fluoroscope axes comprises forming images of fiducial marks attached to the fluoroscope with cameras fixedly connected to the transmitters.

13. The method according to claim 12, wherein introducing the field perturbing element comprises measuring a location and an orientation of the field perturbing element in response to the images of the fiducial marks.

14. Apparatus, comprising:
    a plurality of magnetic transmitters configured to generate a first magnetic field in a region;
    a field perturbing element configured to be introduced into the region; and
    a processor, which is configured to:
    measure the first magnetic field without the field perturbing element within the region;
    characterize multiple images of each magnetic transmitter in the field perturbing element with the field perturbing element in the region,
    calculate a reaction magnetic field in the region based on the characterized images,
    measure a perturbed magnetic field at a probe positioned in the region,
    determine an approximate location of the probe using the perturbed magnetic field;
    calculate a second reaction field at the approximate location of the probe using the first reaction magnetic field;
    subtract the second reaction field from the first magnetic field to determine a second magnetic field; and
    determine a corrected location of the probe in response to the first magnetic field and the second magnetic field.

15. The apparatus according to claim 14, wherein the processor is configured to measure a location and an orientation of the field perturbing element with respect to axes defined by the magnetic transmitters.

16. The apparatus according to claim 15, wherein measuring the location and the orientation of the field perturbing element comprises calculating the location and the orientation adaptively in response to the reaction magnetic field using an optimized cost function.

17. The apparatus according to claim 14, wherein characterizing the multiple images comprises assuming the multiple images are in a predetermined configuration with respect to each other.

18. The apparatus according to claim 17, wherein the predetermined configuration comprises a rectangle and wherein the multiple images comprise five images located at corners and a center of the rectangle.

19. The apparatus according to claim 14, wherein calculating the reaction magnetic field comprises calculating the field according to a spherical harmonic expansion.

20. The apparatus according to claim 19, wherein calculating the reaction magnetic field comprises performing the spherical harmonic expansion up to order 3.

21. The apparatus according to claim 19, wherein calculating the field according to the spherical harmonic expansion comprises configuring the expansion as a spatial transfer matrix, wherein the processor is configured to determine properties of the field perturbing element as a reaction field matrix, and to calculate the reaction magnetic field in response to a product of the spatial transfer matrix and the reaction field matrix.

22. The apparatus according to claim 14, wherein the field perturbing element comprises at least a section of a fluoroscope.

23. The apparatus according to claim 22, and comprising registering fluoroscope-axes, of the fluoroscope, with axes defined by the transmitters.

24. The apparatus according to claim 23, wherein registering the fluoroscope axes comprises forming images of fiducial marks attached to the fluoroscope with cameras fixedly connected to the transmitters.

25. The apparatus according to claim 24, wherein the processor is configured to measure a location and an orientation of the field perturbing element in response to the images of the fiducial marks.

26. A method, comprising:
mounting magnetic transmitters, configured to generate a magnetic field in a patient, on a location pad;
attaching location-pad-cameras with respective fixed orientations to the location pad;
coupling rotatable cameras to the location pad;
attaching fiducial marks to a fluoroscope configured to image the patient;
locating the fluoroscope into different positions; and
for each position:
orienting the rotatable cameras into known orientations, and forming respective images of the fiducial marks with the rotatable cameras and the location-pad cameras, and
analyzing the respective images to register a location and an orientation of the fluoroscope with an axis of the location pad.

27. The method according to claim 26, and comprising removing the rotatable cameras from the location pad, and determining the location and orientation of the fluoroscope with respect to the axis of the location pad using only the images of the fiducial marks formed by the location-pad cameras.

28. The method according to claim 26, wherein attaching the location-pad cameras to the location pad comprises attaching a removable jig to the location pad, and aligning the location-pad cameras to the respective fixed orientations by imaging the jig with the cameras.

29. Apparatus, comprising:
a location pad;
magnetic transmitters, configured to generate a magnetic field in a patient, which are mounted on the location pad;
location-pad-cameras which are attached with respective fixed orientations to the location pad;
rotatable cameras coupled to the location pad;
a fluoroscope configured to image the patient;
fiducial marks attached to the fluoroscope; and
a processor, configured to:
locate the fluoroscope into different positions, and for each position:
orient the rotatable cameras into known orientations, and form respective images of the fiducial marks with the rotatable cameras and the location-pad cameras, and
analyze the respective images to register a location and an orientation of the fluoroscope with an axis of the location pad.

30. The apparatus according to claim 29, wherein the processor is configured, while the rotatable cameras are removed from the location pad, to determine the location and orientation of the fluoroscope with respect to the axis of the location pad using only the images of the fiducial marks formed by the location-pad cameras.

31. The apparatus according to claim 29, and comprising a removable jig which is configured to be attached to the location pad, and wherein the location-pad cameras are configured to align to the respective fixed orientations by imaging the jig with the cameras.

* * * * *